Figure 3:
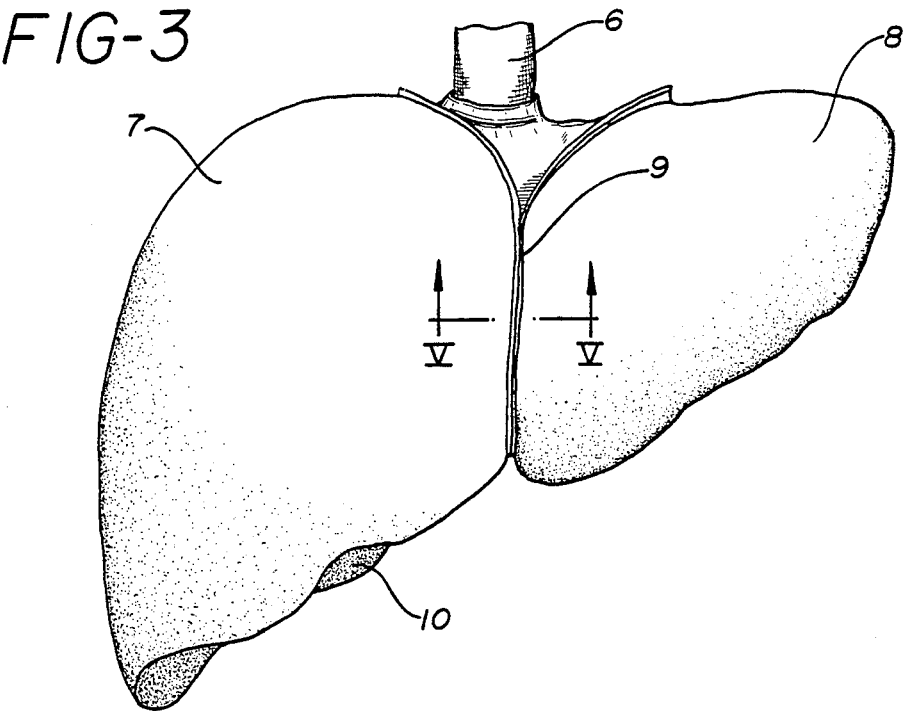

United States Patent [19]
Bilweis

[11] Patent Number: 4,878,890
[45] Date of Patent: Nov. 7, 1989

[54] PERIHEPATIC PROSTHESIS

[75] Inventor: Joseph Bilweis, Noisy le Roi, France

[73] Assignee: Ethicon, Inc., Somerville, N.J.

[21] Appl. No.: 108,385

[22] Filed: Oct. 13, 1987

[30] Foreign Application Priority Data

Oct. 15, 1986 [FR] France ................. 86 14312

[51] Int. Cl.⁴ .............................. A61F 2/02
[52] U.S. Cl. ....................... 600/37; 623/11; 623/66
[58] Field of Search ............. 128/335.5, 156, 98.1, 128/168; 623/1, 11, 12, 66; 260/340.2, 78.3 R; 528/354, 355; 600/37

[56]         References Cited
          U.S. PATENT DOCUMENTS

| 3,949,755 | 4/1976 | Vauquois | 128/335.5 |
| 4,033,938 | 7/1977 | Auguet et al. | 260/78.3 R |
| 4,403,604 | 9/1983 | Wilkinson et al. | 623/12 X |
| 4,428,375 | 1/1984 | Ellman | 128/334 R |
| 4,633,873 | 1/1987 | Dumican et al. | 128/334 R |
| 4,655,221 | 4/1987 | Devereux | 128/334 R |
| 4,693,720 | 9/1987 | Scharnberg et al. | 623/11 |

Primary Examiner—Alan W. Cannon

[57]                ABSTRACT

The present invention relates to a perihepatic prosthesis characterized in that it comprises at least one wing constituted of a central part intended to surround a lobe of the liver and a peripheral fixing part, the said peripheral part having a first transverse edge intended to be fixed on the preliminarily sectioned falciform ligament.

14 Claims, 4 Drawing Sheets

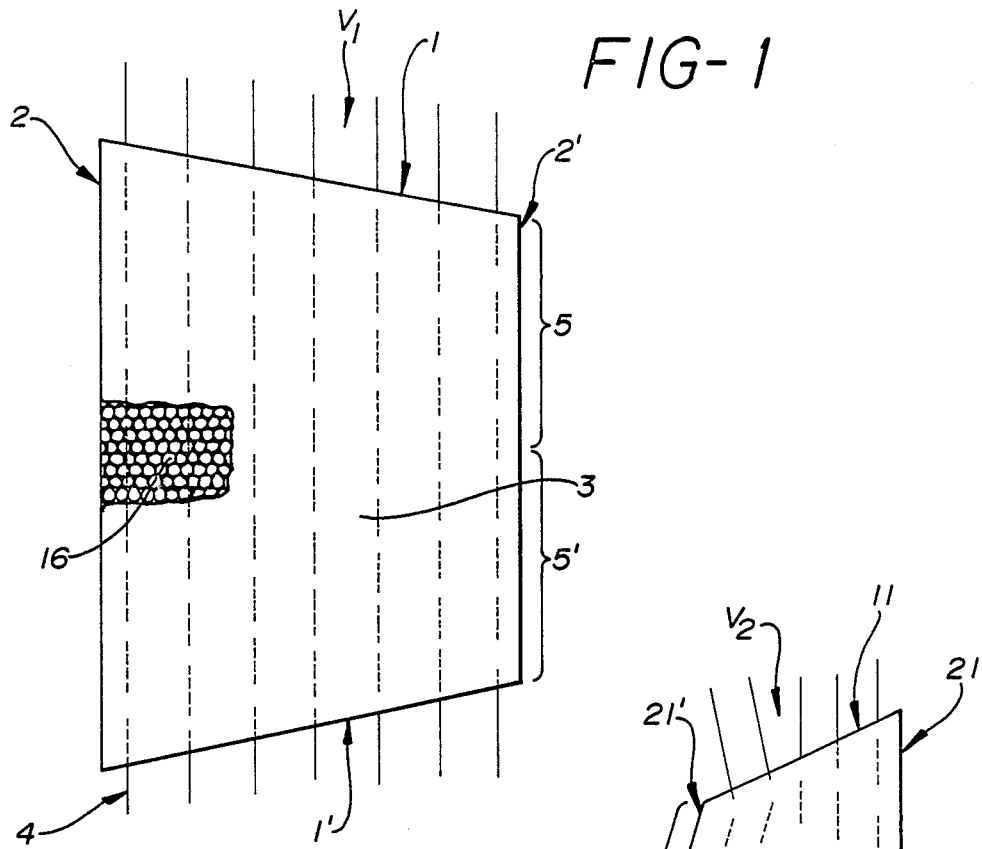
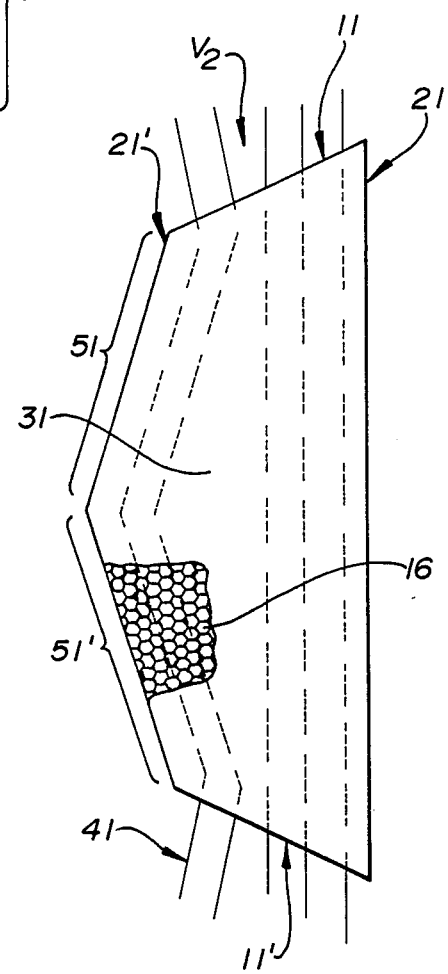

PERIHEPATIC PROSTHESIS

The present invention relates to a perihepatic prosthesis particularly useful for treatment of mechanical lesions of the liver caused by shocks. This type of traumatism is the more frequent because the liver is the most voluminous organ of the body and because of this it is more at risk than the other internal parts of the body.

It is known that the liver usually contains about 60% of its own weight in blood. This high percentage explains the urgency of treatment on wounding of this organ. Now, the connective capsule surrounding the liver, or Glisson capsule is friable. It is thus quickly torn on sudden occurrence of a traumatism. The liver when exposed is very fragile despite its firm consistency; wounded, it bleeds rapidly and profusely. Only a small time is required for emptying the liver of its contents of blood and, without a rapid surgical operation, the liver rapidly loses its functional character.

Further, the liver, because of the multiplicity of its functions, is an organ of such importance that is ineffectiveness rapidly leads to death of the individual.

At present, surgeons are ill equipped for combatting hepatic haemorrhages, although they are more and more successful in combating haemorrhages of other essential organs such as the kidney or spleen.

It has already been proposed for example, to use a knitted surgical mesh for preparation of a pad device intended for repair of injured organs such as the liver (see the specification of European Patent Application No. EP-A-0 159 502).

Now any possible surgical haemostasia of this type is hampered because of the physiological and anatomical peculiarities of the liver which lead to particular problems.

The physiological particularities of the liver are connected to the multiplicity of its functions: First the liver is the organ producing bile. This latter is led via hepatic canals to the gall bladder, the storage organ intimately adhering onto the inner surface of the liver. Further, the liver is the site of a complex and important array of arteries and veins:

oxygenated blood, coming from the aortic artery irrigates the liver via the hepatic artery which divides into two branches, the venous blood coming from all parts of the abdominal cavity is brought together in the portal vein which divides in the liver; thus all the abdominal venous blood passes through the liver, finally, three supra-hepatic veins lead the blood to the lower vena cava which rejoins the right heart.

This abundance of liquid circulating in the liver, arterial blood, abdominal venous blood, hepatic venous blood, bile, explains the seriousness of hepatic laceration.

Surgeons have tried up to now to carry out local compressions for checking haemorrhages. Not only are these local compressions insufficient in the case of a significant lesion but also they can aggravate hepatic traumatisms.

In effect, it is necessary, for maintaining compresses in places for several days, to fix them by various means, particularly filaments of ribbons. These small scale systems very often generate cuts, aggravating the haemorrhage, or ischaemias hindering the return of tissues.

In any case, none of the systems known at present permit rapid and reliable operation which is indispensable in the case of hepatic traumatisms.

A tempting solution, known for the kidney and the spleen for permitting rapid and efficient haemostasia of the organ resides in complete wrapping, holding the organ solidly but without compressing it and thus hindering the blood from flowing whilst permitting the regeneration of the tissues.

But the anatomy of the liver a priori renders this solution impractical. In effect, whilst it is easy to wrap a round or tubular shape such as the kidney or the spleen, the asymmetric and irregular shape of the liver renders wrapping impossible. To its asymmetric form, is to be added the fact that the liver is not an organ isolated form others in the abdomen being on the contrary solidly held in place, and connected to part of the diaphragm by:

the lower vena cava, a sort of large fastening column for this organ, the falciform ligament or suspension ligament which connects the upper face of the liver to the diaphragm and to the abdominal wall, and divides this organ into a right lobe and left lobe, triangular or coronary ligaments on the rear face of the liver which connect this to the lower face of the diaphragm.

This is why the known solution of wrapping is not applicable as such in the case of the liver.

The present invention propose a new prosthesis permitting by its own structure provision of such a wrapping profitting from the anatomical particularities of the liver which appear to the man skilled in the art as insurmountable obstacles.

More precisely, the present invention proposes a perihepatic prosthesis provided in biodegradable supple surgical material having at least one wing constituted by a central part intended to surround a lobe of the liver, and by a peripheral fixing part, the said peripheral part having a first transverse edge intended to be fixed on the preliminarily sectioned falciform ligament.

This peripheral part is thus able to hold the wing around the lobe whilst fastening it to the preliminarily sectioned falciform ligament.

Preferably, the peripheral part comprises in addition to this first transverse edge intended to be fixed on the falciform ligament:

a second transverse edge, opposite from the first, able to be bent back on itself in the form of two symmetric segments, the two symmetric segments being intended to be attached to each other, two lateral edges opposite each other, connecting the two transverse edges, and intended to be attached to each other.

Preferably, also, the prosthesis comprises a wing (a principal wing) intended for the right hepatic lobe and a wing (an auxiliary wing) intended for the left hepatic lobe.

Such a structure is particularly suitable for responding to the problems posed.

As previously mentioned, the falciform ligament which is found on the upper surface of the liver is an aponeurotic limit separating the two lobes of the liver: the right lobe, so voluminous that it will be designed by the term "right liver" in the rest of the description; the left lobe, much smaller, called "left liver" below. Now, it has been noticed that, surprisingly, this falciform ligament, as well as the triangular and coronary ligaments, are in fact only embryonic residues, not determinative of the position of the liver. When these filaments are cut, the liver remains in position and then becomes an organ anatomically isolated from the others, and "fastened" as it were at a large column which is constituted by the lower vena cava.

The applicant has realised that one can thus get round the anatomical problems (the asymmetric shape) and the physiological problems of the liver by positioning a prosthesis having a principal wing and/or an auxiliary wing which is fixed on the preliminarily sectioned falciform ligament, each of the two wings being able to be positioned independently of the other.

This ligament proves to constitute, after its separation by cutting from the diaphragm, a sort of band able to serve as an anchorage for the prosthesis according to the invention.

A major physiological problem is also surmounted, according to the invention, because the bile duct and biliary canals are covered up by the principal wing which thus avoids the bile spilling into the abdomen and permits the regeneration of the tissues constituting the gall bladder and biliary canals, often injured in a hepatic traumatism.

The prosthesis according to the present invention can be provided in many surgical materials, but preferably, it is provided in a supple and biodegradable material of the tissue type or knitted which will be designated by "network" in the rest of the description.

By "network" is intended any product having a generally similar structure to that of a gauze, obtained by assembly of filaments which will advantageously be of the same nature as the ligature or suture filaments usually used in surgery, the assembly of these filaments being able to be carried out by any known means such as plaiting, weaving, assembly by knitting or crochet for example.

Such networks find their applications amongst others in the treatment of large visceral exposures for which they permit the keeping alive of organs or in the conversation treatment of traumatic kidneys and spleens.

These networks have generally satisfactory qualities of tolerance by the body, mechanical strength and speed of reabsorption. Further, the permeability of the absorbable network positioned for efficaceously containing the organs, constitute a further asset since it permits the draining of serosities and excretion products normally flowing from a newly treated wound.

Finally, the mesh of the network used according to the present invention is sufficiently resistant to be able to be fixed on the falciform ligament without it being necessary for it to be covered up by reinforcements in this area.

In accordance with a preferred embodiment of the invention, the surgical material consists of a network of reabsorbable synthetic filaments based on a polymer of glycolic acid.

In accordance with a preferred embodiment of the invention, the reabsorbable synthetic filaments of the said network are of a copolymer of glycolic acid and lactic acid. Preferably there will be used a VICRYL (Registered Trade Mark) network—polyglactine 910 which is a copolymer having approximately 90% of glycolic acid and approximately 10% of lactic acid.

Each of the wings of the prosthesis according to the invention is preferably of the form adapted to the hepatic lobe for which it is intended. Preferably also, each of the wings has standard dimensions able to be adapted to individual variations, the dimensions of the liver varying of course from one individual to another.

Figure 4:
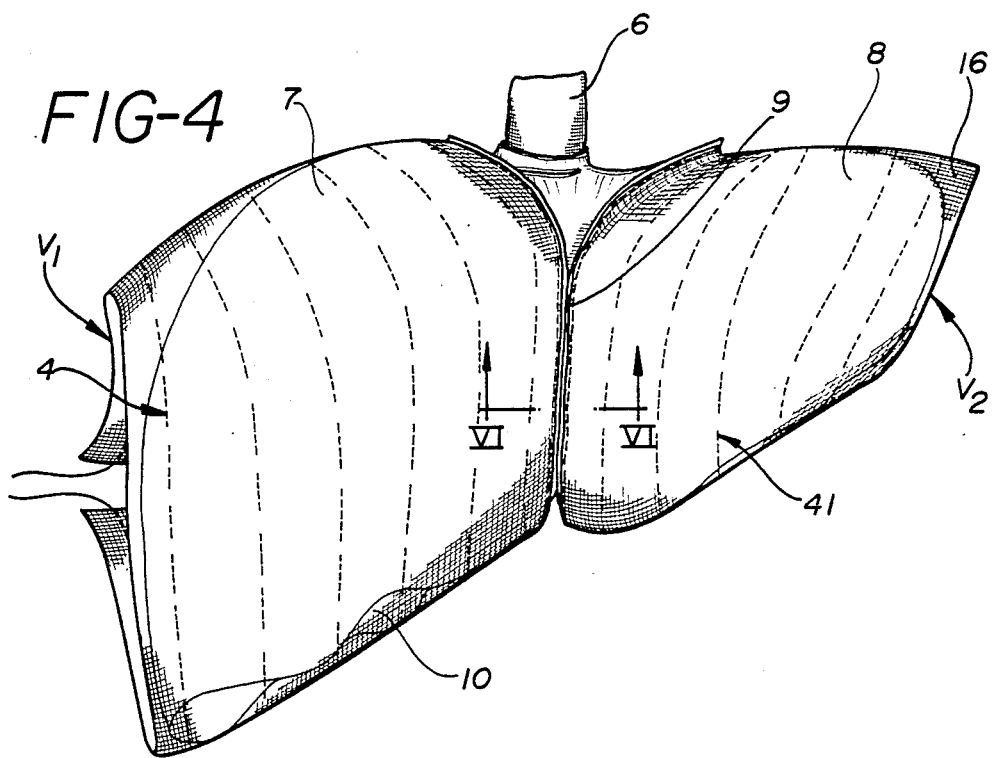
Figure 5:
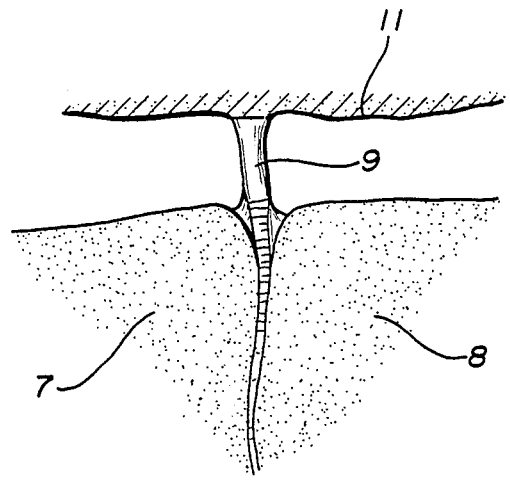
Figure 6:
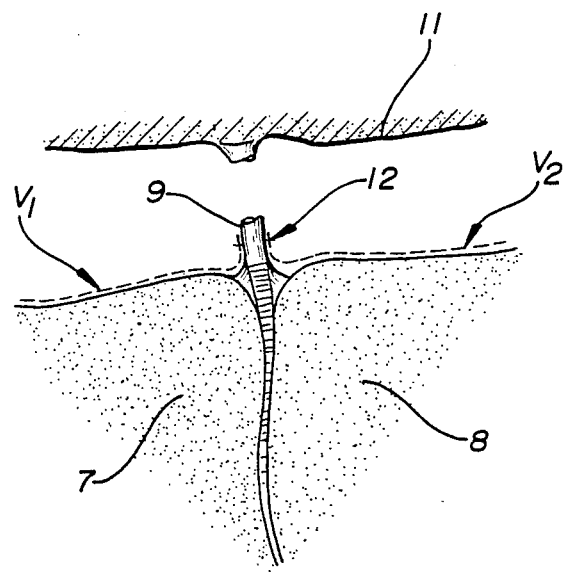
Figure 7:
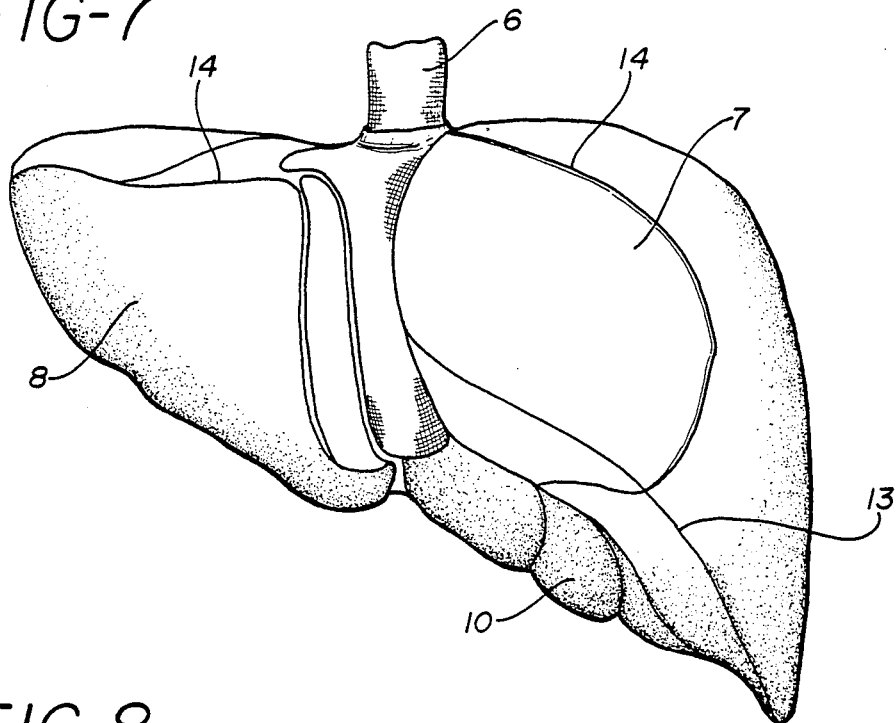
Figure 8:
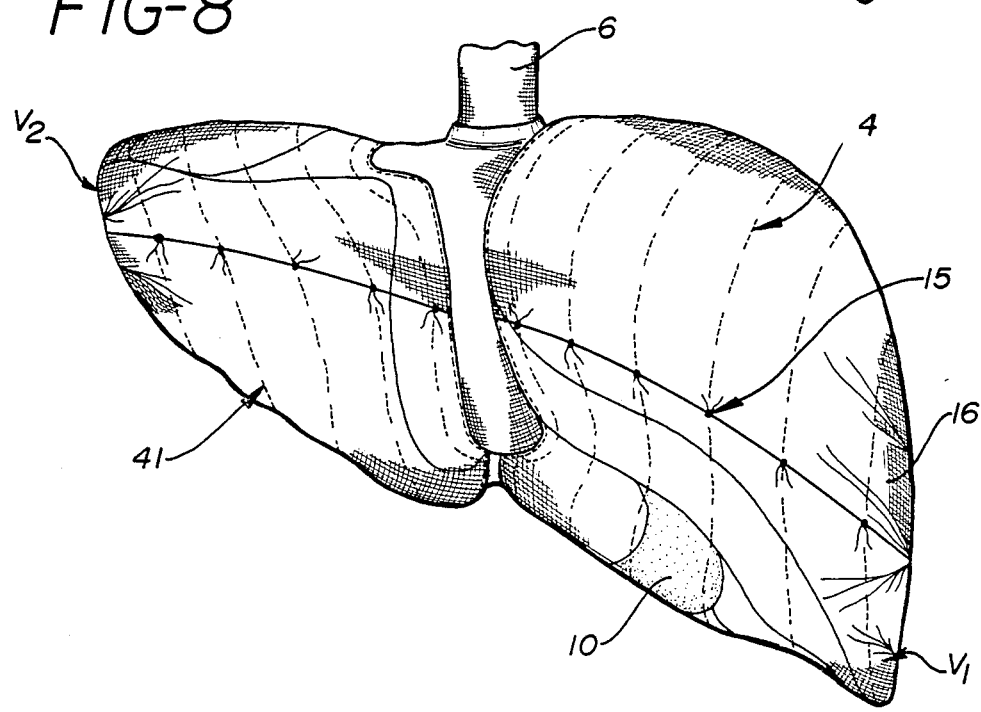

The shapes and dimensions of the prosthesis according to the present invention as well as the method for positioning one or other of the constituents wings of the prosthesis will appear from the following description and accompanying drawings. In the accompanying drawings:

FIG. 1 shows the principal wing laid flat;
FIG. 2 shows the auxiliary wing also laid flat;
FIG. 3 shows the front face of the liver;
FIG. 4 shows the front face of the liver covered up by the perihepatic prosthesis according to the invention;
FIG. 5 shows a cross-section on line V-V of FIG. 3, in which is partially shown the diaphragm which is not visible in FIG. 3;
FIG. 6 shows a cross-section on line VI-VI of Figure 4 in which is partially shown the diaphragm not visible in FIG. 4;
FIG. 7 shows the rear face of the liver;
FIG. 8 shows the rear face of the liver covered up by the perihepatic prosthesis according to the invention.

The prosthesis of FIGS. 1 and 2 represents a preferred embodiment of the invention.

The principal wing $V_1$ (FIG. 1), that is to say that of which the central part 3 is intended to surround the right liver, is in the shape of an isosceles trapezium. In its peripheral part, its longer base 2 constitutes the first transverse edge intended to be fixed on the falciform ligament, and the shorter base 2' constitutes the second transverse edge intended to be bent back on itself in the form of two segments 5 and 5'. The two segments 5 and 5' are symmetrical with respect to the bisector of the two bases of the trapezium. The longer base 2 has, preferably, a length between 40 and 50 cm, the ideal dimension being approximately 44 cm. The height of this trapezium, between 25 and 35 cm, is, preferably, approximately 30 cm. The shorter base 2' has a length between 28 and 38 cm, and is preferably approximately 33 cm.

The two lateral edges 1 and 1', corresponding to the two non parallel sides of the trapezium, have a length between 21 and 41 cm, equal preferably to approximately 31 cm.

The auxiliary wing $V_2$ (FIG. 2), that is to say that of which the central part 31 is intended to surround the left liver, is preferably of convex pentagonal shape of which a segment 21, longer longer than the others, represents a first transverse edge, that is to say that which is intended to be fixed on the falciform ligament. This first transverse edge 21 measures between 45 and 55 cm, and is preferably approximately 50 cm long. The pentagon has symmetry with respect to the bisector of this side 21. The bisector, of which the length is between 20 and 26 cm, preferably measures approximately 21 cm. The two lateral edges 11 and 11' intended to be attached to each other, have a length between 11 and 21 cm, which is preferably equal to 16 cm.

As regards the second transverse edge 21', intended to be bent back on itself, it is in the form of two symmetrical segments 51 and 51', each of these segments measuring between 16 and 26 cm, preferably 21 cm.

The principal $V_1$ and auxiliary $V_2$ wings have been shown on the same sheet, at the same scale, and opposite to each other, in a manner to represent the way they are arranged on the liver, when positioned in a prosthesis according to the invention.

The mesh of the constituent network of each of the two wings is shown partially at 16, but of course the entire wings are of a material having a mesh of this type.

FIGS. 3 and 7 show respectively the front and rear faces of the liver.

In these Figures, there is schematically shown the left 8 and right 7 lobes of the liver, the lower vena cava 6 and the gall bladder 10.

The falciform ligament 9 connects the front face of the liver to the diaphragm 11 and thus to the abdominal wall as is shown schematically in FIG. 5 (cross-section V—V).

The triangular 13 and coronary 14 ligaments constitute a conjuctive tissue connecting the rear face of the liver to the diaphragm.

FIGS. 4 and 8 show the front and rear faces of the liver respectively, these faces being covered by the prosthesis according to the present invention.

For positioning the prosthesis according to the present invention, one can use a variety of surgical fixing means. In particular, the fixing of the first transverse edge 2,21 on the falciform ligament 9 can be made by means of clips or of whippings 12 after cutting of the said ligament as shown in FIG. 6. This first transverse edge 2,21 being fixed, the right liver and the left liver, respectively, are surrounded and the two lateral edges 1 and 1', 11 and 11' of the prosthesis are fixed to each other. This fixing can also be made by means of clips or whippings. Preferably the prosthesis according to the present invention comprises transverse rows of surgical filaments 4,41, passed into the wing. These filaments are principally intended to compress the hepatic lobe after surrounding and tightening. If need be, the filaments can also be used to attach the two lateral edges 1 and 1', 11 and 11' to each other.

In the case of the principal wing, the filaments 4 are arranged parallel to the two bases 2 and 2' of the trapezium (FIG. 1). In the case of the auxiliary wing $V_2$ these filaments 41 are arranged:

parallel to the first transverse edge 21 in a corresponding zone of the auxiliary wing $V_2$, that is to say the zone close to the said first transverse edge 21, parallel to each of the two segments 51 and 51' forming the second transverse edge 21' in the part intended to surround the edge of the left liver (FIG. 2). The filaments are advantageously placed on the prosthesis by the manufacturer of the prosthesis (and not by the surgeon).

The useful network of the prosthesis according to the invention has "ladderproof" mesh when they are crossed by these surgical filaments. These filaments 4 and 41 are arranged at variable intervals between 2 and 12 cm, preferably 5 to 6 cm. Preferably also, filaments are used of which the colour permits them to be easily visible when they are positioned on an organ which is bleeding, such as violet or colourless, and, for easy manipulation, the colour of these filaments alternate. These filaments are intended to be knotted to each other, on positioning of the prosthesis (FIG. 8). Simple knots 15 can be made or slip knots, these latter permitting progressive tightening of the perihepatic prosthesis around the liver. These filaments are simply passed across the meshes of the network and, for rapid manipulation, are knotted together at their exits from the network, before use of the prosthesis.

The prosthesis according to the present invention preferably has a colour adapted to its use such as its natural colour.

The positioning of the prosthesis will be easy to understand with reference to the accompanying drawings.

It has already been mentioned above that each of the wings $V_1$ and $V_2$ can be positioned independently of the other.

Thus, by way of example, the positioning of the principal wing $V_1$ will preferably be carried out according to the invention in the following manner:

After disengaging the liver from the surrounding organs by cutting of the falciform 9, triangular 13 and coronary 14 ligaments, the surgeon slides the central part 3 of the principal wing $V_1$ under the right liver 7, so that the longer base 2 is at the centre of the liver. He fixes this first transverse edge 2 along the length of the falciform ligament 9 by means of clips 12, and then surrounds the right liver 7 with the central part 3. He provisionally attaches the lateral edges 1 and 1' to each other by means of surgical pincers. Then he turns back on itself the second transverse edge 2' in the form of two symmetrical segments 5 and 5' which he attaches to each other provisionally with surgical pincers. The right liver 7 is thus immediately haemostasised.

Then the surgeon knots one at a time by simple knots 15, the surgical filaments 4 preliminarily threaded in the network. The two lateral edges 1 and 1' of the principal wing are thus definitively attached to each other. As regards the two symmetrical segments 5 and 5' comprising the second transverse edge 2', they are definitively fixed to each other by means of surgical whippings or clips. The positioning of the auxiliary wing $V_2$ is then carried out in a similar manner.

Once in position, the prosthesis according to the present invention acts for approximately two to three weeks after which it is progressively reabsorbed. Now, three or four days is sufficient for a haemostasia of the liver. The resistance of the network used in thus largely sufficient for permitting the regeneration of the hepatic tissues.

I claim:

1. A perihepatic prosthesis of a supple biodegradable surgical material for haemostasizing a hepatic lobe of a liver, comprising:
    at least one wing constituted of a central part dimensioned in the shape of an isosceles trapezium for surrounding a hepataic lobe of a liver and including
    a first peripheral fixing part comprising the longer base of said trapezium intended to be fixed on a falciform ligament of said liver, said longer base being suitable for substantially surrounding said liver proximate the jointure of said hepatic lobe with a second hepatic lobe of said liver;
    a second peripheral fixing part comprising the shorter base of said trapezium opposing said longer base; and
    first and second lateral edges comprising the non parallel sides of said trapezium and disposed between said longer and shorter bases and being suitable for enclosing said hepatic lobe within said prosthesis along a line extending from said remote end of said hepatic lobe to said longer base.

2. A perihepatic prosthesis according to claim 1, wherein said shorter base of said trapezium is
    able to be bent back on itself in the form of two symmetric segments, said two symmetric segments being intended to be attached to each other to enclose the end of said hepatic lobe remote from said jointure;

and wherein said non parallel sides are opposite each other and are intended to be attached to each other.

3. A perihepatic prosthesis according to claim 1, comprising in combination one said wing intended for a right hepatic lobe of said liver and another said wing intended for a left hepatic lobe of said liver.

4. A prosthesis according to claim 1, wherein said material comprises a network of reabsorbable synthetic filaments particularly based on a copolymer of glycolic acid and lactic acid.

5. A prosthesis according to claim 2, wherein said wing is intended for a right hepatic lobe of said liver and is in an isosceles trapezium shape of which a longer base constitutes said first transverse edge and a shorter base constitutes said second transverse edge.

6. A prosthesis according to claim 5, wherein said trapezoidal shape possesses the following dimensions:
base between 40 and 50 cm,
base between 28 and 38 cm,
height between 25 and 35 cm.

7. A prosthesis according to claim 2, wherein said wing is intended for a left hepatic lobe and is of a convex pentagon shape of which a segment, longer than each of four others, constitutes said first transverse edge, of which two segments adjacent to said first transverse edge form said two lateral edges and of which two last segments adjacent each other form said second transverse edge.

8. A prosthesis according to claim 7, having the following dimensions:
length of said first transverse edge between 45 and 55 cm,
length of each of said two segments adjacent each other constituting said second transverse edge between 16 and 26 cm,
length of each of said two lateral edges between 11 and 21 cm.

9. A prosthesis according to claim 1 including transverse rows of spaced apart securing filaments passed into said wing and separated from one another by areas of said material and intended to compress said hepatic lobe after surrounding and tightening.

10. A prosthesis according to claim 8, wherein said filaments are also intended to attach the two non parallel sides to each other.

11. A prosthesis according to claim 9, wherein said filaments have colors which alternate from one spaced apart filament to the next.

12. A prosthesis according to claim 1, wherein said wing further includes a triangular section of said supple biodegradable surgical material with the base of said triangular section being aligned with said shorter base of said isosceles trapezium,
wherein the sides of said triangular section are suitable for overlapping each other for enclosing the end of said hepatic lobe remote from said jointure.

13. A prosthesis according to claim 12, comprising in combination one said wing intended for a right hepatic lobe of said liver and another said wing intended for a left hepatic lobe of said liver.

14. A prosthesis according to claim 12 including transverse rows of spaced apart securing filaments passed into said wing, a first group of said filaments extending generally parallel to said longer base and a second group of said filaments extending generally parallel to said sides of said triangular section.

* * * * *

UNITED STATES PATENT AND TRADEMARK OFFICE
CERTIFICATE OF CORRECTION

PATENT NO. : 4,878,390

DATED : November 7, 1989

INVENTOR(S) : Joseph Bilweis

It is certified that error appears in the above-identified patent and that said Letters Patent is hereby corrected as shown below:

Claim 10, column 8, line 11 "A prosthesis according to claim 8" should read -- A prosthesis according to claim 9 --.

Signed and Sealed this

Twenty-third Day of October, 1990

Attest:

HARRY F. MANBECK, JR.

*Attesting Officer*     *Commissioner of Patents and Trademarks*